(12) United States Patent
Mori et al.

(10) Patent No.: US 9,429,125 B2
(45) Date of Patent: Aug. 30, 2016

(54) SPRAY MEASURING METHOD AND SPRAY TEST APPARATUS USED IN THE METHOD

(75) Inventors: Sachio Mori, Mishima (JP); Tatsuo Kobayashi, Susono (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 240 days.

(21) Appl. No.: 14/005,646

(22) PCT Filed: Apr. 26, 2011

(86) PCT No.: PCT/JP2011/060138
§ 371 (c)(1),
(2), (4) Date: Sep. 17, 2013

(87) PCT Pub. No.: WO2012/147158
PCT Pub. Date: Nov. 1, 2012

(65) Prior Publication Data
US 2014/0033810 A1 Feb. 6, 2014

(51) Int. Cl.
*G01N 15/02* (2006.01)
*F02M 65/00* (2006.01)
*G01N 33/44* (2006.01)

(52) U.S. Cl.
CPC .......... *F02M 65/00* (2013.01); *G01N 15/0266* (2013.01); *G01N 33/442* (2013.01); *F02M 65/001* (2013.01)

(58) Field of Classification Search
None
See application file for complete search history.

(56) References Cited

U.S. PATENT DOCUMENTS

| 3,275,744 | A | * | 9/1966 | Dietrich | 348/132 |
| 6,053,037 | A | * | 4/2000 | Kojima et al. | 73/114.46 |
| 6,298,719 | B1 | * | 10/2001 | Schoeffel et al. | 73/114.46 |
| 6,508,112 | B1 | * | 1/2003 | Verhoeven | 73/114.46 |
| 2014/0007661 | A1 | | 1/2014 | Kobayashi | |

FOREIGN PATENT DOCUMENTS

| JP | 01-036055 B2 | 7/1989 |
| JP | 2010-084249 A | 4/2010 |
| WO | 2012/131935 A1 | 10/2012 |

* cited by examiner

*Primary Examiner* — Robert R Raevis
(74) *Attorney, Agent, or Firm* — Sughrue Mion, PLLC

(57) ABSTRACT

Test liquid (3) including thermosetting resin is injected from an injection valve (2). Light (L) is irradiated to a spray (6) of the test liquid (3) injected from the injection valve (2) as a treatment for producing a hardening effect to the thermosetting resin. Liquid drops in the spray (6) are hardened and collected as particles. Spray characteristics such as a particle size distribution of the injection valve or the like are analyzed by using the collected particles.

17 Claims, 6 Drawing Sheets

100# SPRAY MEASURING METHOD AND SPRAY TEST APPARATUS USED IN THE METHOD

CROSS REFERENCE TO RELATED APPLICATIONS

This application is a National Stage of International Application No. PCT/JP2011/060138 filed Apr. 26, 2011, the contents of all of which are incorporated herein by reference in their entirety.

TECHNICAL FIELD

The present invention relates to a method and an apparatus for measuring spray characteristics of, for example, a fuel injection valve in an internal combustion engine or the like.

BACKGROUND ART

In order to improve performance of a fuel injection valve in an internal combustion engine, it is necessary to assess spray characteristics such as a diameter distribution of fuel liquid drops contained in the spray and separation states of liquid and gas phases. As methods of counting the number of ultrafine particles suspended in air, there is known a method including coarsening fine particles through condensation under oversaturated atmosphere and optically counting the number of coarsened fine particles (for example, see Patent Literature 1). In addition, there is Patent Literature 2 as a prior art reference in relation to the present invention.

CITATION LIST

Patent Literature

Patent Literature 1: JP-01-036055B
Patent Literature 2: JP-2010-084249A

SUMMARY OF INVENTION

Technical Problem

In a conventional counting method of fine particles, since measurement is made in a liquid state, measurement methods are limited and it is difficult to make high-precision measurement. In view of the foregoing, an object of the present invention is to provide a spray measurement method of measuring spray characteristics of an injection valve in a different way from conventional measurement methods and provide a spray test apparatus suitably used in the method.

Solution to Problem

A spray measurement method of the present invention comprises a step of injecting test liquid including curable resin from an injection valve; a step of hardening liquid drops in a spray of the test liquid injected from the injection valve into particles by applying treatment for producing a hardening effect of the curable resin; and a step of analyzing spray characteristics of the injection valve using the particles hardened.

According to the spray measurement method of the present invention, by applying the treatment for producing the hardening effect of the curable resin in the test liquid to the spray injected from the injection valve, it is possible to be hardened the liquid drops in the spray into particles. Since the hardened particles may be considered to be substantially identical to the liquid drops in the spray, it is possible to execute analysis of spray characteristics from various perspectives, such as measurement of diameters of the liquid drops or measurement of a particle size distribution of the particle groups, by using obtained particles.

In the measurement method of the present invention, in the step of hardening, the treatment for producing the hardening effect is applied to the spray which is obtained in the step of injecting test liquid from an injection valve. Accordingly, the step of hardening is executed concurrently with a period which is at least a part of the step of injecting. The treatment for producing the hardening effect may be determined depending on the curable resin selected. The step of analyzing may be executed after collecting hardened particles. Furthermore, the step of analyzing may be executed concurrently with the step of hardening so that the hardened particles are analyzed sequentially.

In one embodiment of the spray measurement method of the present invention, the curable resin may be a resin in which a hardening effect is produced by irradiation of an energy beam, and the energy beam may be irradiated to the spray as the treatment in the step of hardening. According to this embodiment, by irradiating the energy beam to the spray, the hardening effect is produced to the liquid drops in the spray and it is possible to obtain the particles. The energy beam refers to types of beams which can produce the hardening effect by being irradiated to the curable resin. The energy beam includes, for example, a light beam such as an infrared ray, a visible light, an ultraviolet ray, etc., an electron beam, a radiation, heat-ray, or the like.

Furthermore, a thermosetting resin may be used as the curable resin, and light having a specific wavelength range may be used as the energy beam. By being absorbed the light into the liquid drops and increasing a temperature thereof, the thermosetting resin in the liquid drops is hardened. Thereby, a gas phase and a liquid phase in the spray may be clearly separated from each other. By appropriately combining irradiation conditions such as a wavelength region of the light, intensity, etc., and types of thermosetting resins, it is possible to suitably adjust a hardening rate of the liquid drops or the like. In addition, it is easy to make a setting such as limiting an irradiation range of the light in a part of the spray. Thereby, it is possible to promote further diversification in measurement methods.

The irradiation of the energy beam to the spray may be set to a partial region of the spray with respect to an injecting direction of the test liquid from the injection valve. According to this aspect, it is possible to harden the liquid drops by focusing the energy beam on a specific range of the spray in the injecting direction, for example, an area near an injection port or a front end of the spray. And, by using obtained particles, it is possible to analyze the spray characteristics in the specific range of the spray. Furthermore, while an irradiating position of the energy beam may be changed along the injecting direction, the particles may be analyzed each time the irradiating position being changed. In this case, the spray characteristics can be analyzed in conjunction with a position of the spray. By comparison between analysis results at multiple positions, a positional variation of spray characteristics can be analyzed.

Otherwise, irradiation time of the energy beam may be limited to a part of a period when the spray of the test liquid exists. According to this aspect, the spray characteristics can be analyzed in conjunction with a specific time of a part of a period when the spray exists. Furthermore, at least a part of the period when the spray of the test liquid exists may be divided into several irradiation times, the energy beam may be irradiated for each irradiation time, and the particles may be analyzed separately for each divided irradiation time. According to this aspect, the spray characteristics can be analyzed depending on respective irradiation times in the period when the spray exists. By comparison between analyzed results in different times with each other, a variation in the spray characteristics with respect to time may also be analyzed.

The spray measurement method of the present invention may further comprise a step of charging the test liquid including the curable resin before applying the treatment to the spray. In this case, in the step of hardening the liquid drops, an electric field may be made to generate in a direction orthogonal to the injecting direction of the test liquid. According to this aspect, since the liquid drops in the spray of the test liquid are charged, particles which are obtained by hardening the liquid drops are also charged. Thereby, a moving direction of the particle is curved toward a direction of the electric field. According to the extent of such curving, there is a difference in positions in the injecting direction of particles in the electric field. The extent of curving by the electric field is a function of a mass and velocity of the particle, wherein the mass of the particle is determined by a diameter of the particle. Accordingly, it is possible to determine a velocity distribution of the particles based on a positional distribution of the particles in the injecting direction and the diameter of the particle.

In addition, in the step of hardening the liquid drops, the particles, a moving direction of which is curved by the electric field, may be collected by being adsorbed and held on a holding part, the holding part being located along the injecting direction, and in the step of analyzing the spray characteristics, a distribution on the holding part and diameters of collected particles may be measured, and a velocity distribution of the particles may be determined based on the distribution and diameters of the particles obtained. According to this aspect, the positional distribution of the particles curved by the electric field is held on the holding part. Accordingly, by measuring the distribution of the particles and the diameters of the particles using a method such as a photographing of the particles on the holding part, it is possible to determine the velocity distribution of the particles easily.

In the present invention, it is possible to employ injection valves of various uses in the test. For instance, a fuel injection valve of an internal combustion engine may be employed in the test. In this case, the test liquid may be prepared by mixing the curable resin with fuel of the internal combustion engine. According to this aspect, it is possible to measure spray characteristics of the fuel injected from the fuel injection valve according to the present invention.

A spray test apparatus of the present invention comprises a test liquid supply device which is configured to supply a test liquid including curable resin to a injection valve; and a hardening device which is configured to harden liquid drops in a spray of the test liquid injected from the injection valve into particles by applying treatment for producing a hardening effect to the curable resin, to the spray.

According to the spray test apparatus of the present invention, by supplying the test liquid from the test liquid supply device to the injection valve and injecting the test liquid, and hardening the liquid drops in the spray from the injection valve by the hardening device, it is possible to obtain particles which are considered to be substantially identical to the liquid drops in the spray. By using the obtained particles, it is possible to execute analysis of spray characteristics from various perspectives, such as measurement of diameters of the liquid drops or measurement of a particle size distribution of the particle groups.

In one embodiment of the spray test apparatus of the present invention, the test liquid supply device may be configured to supply to the injection valve the test liquid containing the curable resin in which a hardening effect is produced by irradiation of an energy beam, and the hardening device may be configured to irradiate the energy beam to the spray as the treatment. According to this embodiment, by irradiating the energy beam to the spray, it is possible to produce the hardening effect to the liquid drops in the spray and obtain the particles. The meaning of the energy beam is the same as described above. Furthermore, the test liquid supply device may be configured to supply thermosetting resin, as the curable resin, to the injection valve, and the hardening device may be configured to irradiate light having a specific wave length range as the energy beam. According to this aspect, as described above, it is possible to harden the liquid drops by increasing a temperature of the liquid drops in the spray.

The hardening device may be configured so that the irradiation of the energy beam is limited to a part of the spray in an injecting direction of the test liquid from the injection valve. According to this aspect, by focusing the energy beam on a specific range of the spray in the injecting direction and hardening the liquid drops, it is possible to measure the spray characteristics in the specific range. Furthermore, the hardening device may be configured to be capable of changing an irradiating position of the energy beam along the injecting direction. According to this aspect, it is possible to execute the analysis the particles separately for every irradiating position while altering the irradiating position along the injecting direction.

Otherwise, the spray test apparatus of the present invention may further comprises an irradiation time control device which is configured to restrict irradiation time of the energy beam to at least a part of a period when the spray of the test liquid can exist. According to this aspect, it is possible to measure the spray characteristics in conjunction with a specific time in the period when the test liquid exists. Furthermore, when the irradiation time is altered, the particles are separated and the spray characteristics are analyzed each time the irradiation time being altered. And, by comparison between analyzed results, a variation in the spray characteristics with respect to time can be analyzed.

The spray test apparatus of the present invention may further comprises a charging device which is configured to charge the test liquid including the curable resin, and an electric field generation device which is configured to generate an electric field in a direction orthogonal to the injecting direction of the test liquid. According to this aspect, the charged test liquid can be injected from the injection valve and a moving direction of the hardened particle can be curved in a direction of the electric field depending on the diameter and the velocity of the particle. Thereby, it is possible to make a difference in positions in the injecting direction of particles in the electric field. Accordingly, it is possible to determine a velocity distribution of the particles by obtaining a positional distribution and a diameter of the particle.

The electric field generation device may have a pair of electrodes arranged to face each other so that a region where the test liquid is injected is interposed in a direction orthogonal to the injecting direction, and the electrode having opposite polarity to a charge of the test liquid, may be provided with a holding part adsorbing and holding particles, a moving direction of the holding particles being curved by the electric field. According to this aspect, a positional distribution of the particles curved by the electric field can be held on the holding part. And, it is possible to determine the velocity distribution of the particles by measuring the distribution and diameters of the particles on the holding part.

DESCRIPTION OF EMBODIMENTS

First Embodiment

Figure 1:
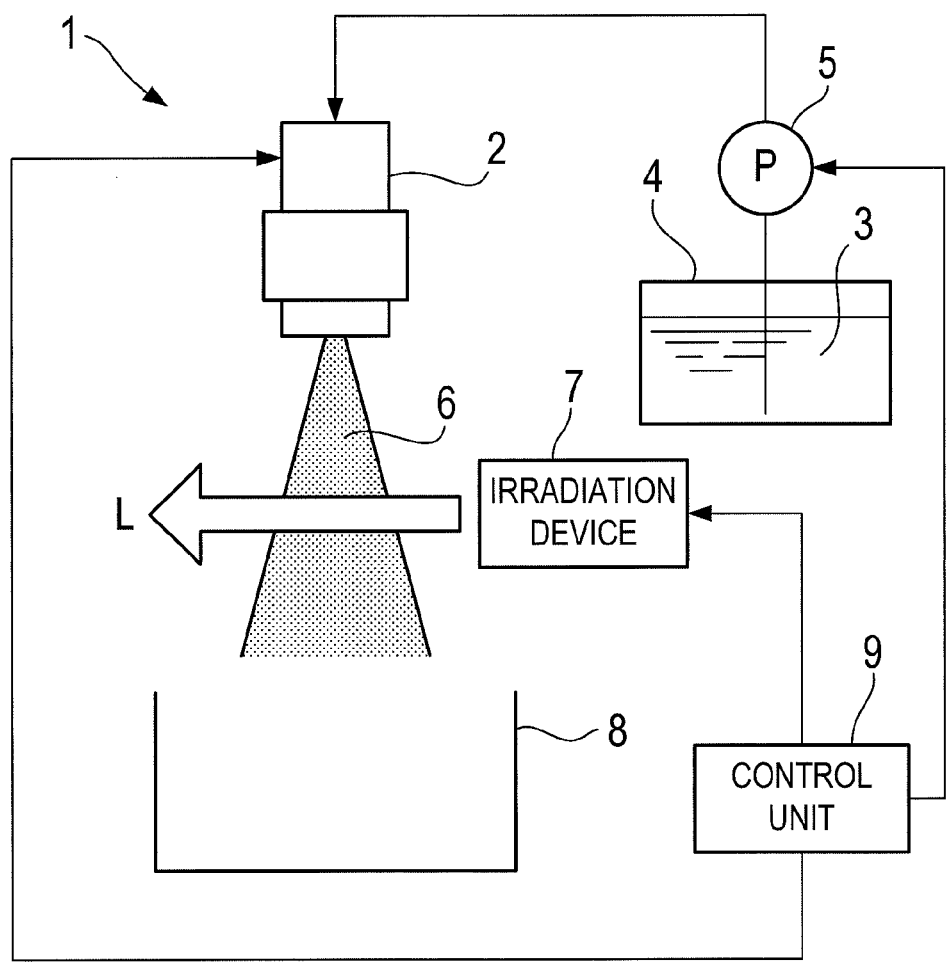
FIG. 1 is a diagram showing a test apparatus according to a first embodiment of the present invention.

First, with reference to FIG. 1, a configuration of a test apparatus to be used in a spray measuring method according to a first embodiment of the present invention will be described. The test apparatus 1 includes a tank 4 to receive test liquid 3 injected from a fuel injection valve 2 as a test target, a pump 5 to pressurize the test liquid 3 in the tank 4 to a predetermined fuel injection pressure and to provide the test liquid 3 to the fuel injection valve 2, an irradiation device 7 to irradiate light L having a specific wavelength region (e.g., an ultraviolet region) to a spray 6 of the test liquid injected from the fuel injection valve 2, and a collection container 8 to collect the spray 6 after the light L is irradiated. The fuel injection valve 2 may be, for example, a fuel injection valve to inject the fuel to an intake air of an internal combustion engine for a vehicle. The tank 4 and the pump 5 function as a test liquid supply device to supply the test liquid 3 to the fuel injection valve 2. It is enough that the tank 4 can store the test liquid 3 in an amount necessary for measuring spray characteristics. Any pump may be appropriately selected as the pump 5 as long as it can pressurize the test liquid 3 to the fuel injection pressure. A pressure accumulation part such as an accumulator for accumulating the pressurized test liquid 3 may be provided between the pump 5 and the fuel injection valve 2.

The test liquid 3 is prepared by mixing predetermined curable resin with the fuel to be injected from the fuel injection valve 2. Thermosetting resin which is generally in a liquid state, and hardened by heating, may be used as the curable resin. As one example, thermosetting resins such as a melamine resin, a urea resin, or the like is applied to the curable resin. The irradiation device 7 irradiates the light L having the specific wavelength region (e.g., the ultraviolet region), the light L being formed in a predetermined shape, toward the spray 6 as treatment of producing a hardening effect in the curable resin. Since the fuel contained in the test liquid 3 has color, energy of the light L is absorbed into liquid drops in the spray 6 and is converted into heat when the spray 6 is irradiated with the light L. The temperature of the liquid drops is raised by the heat, and the thermosetting resin hardens. Thereby, particles (or microparticles) corresponding to the liquid drops are generated. In other words, the irradiation device 7 functions as a hardening device by irradiating the light L to the spray 6 as the treatment of producing the hardening effect in the thermosetting resin contained in the test liquid 3. In order to harden the liquid drops in the spray 6, the thermosetting resin needs to have a hardening rate at which hardening occurs in the spray 6 in response to the irradiation of the light L. In order to improve precision in measurement of spray characteristics, it is preferable to control types of resin or a mixing ratio thereof such that physical properties of the test liquid 3 containing the thermosetting resin are not significantly different from physical properties of the fuel to be actually injected from the fuel injection valve 2.

An irradiation direction of the light L by the irradiation device 7 is set to a direction (a horizontal direction in FIG. 1) orthogonal to the injecting direction of the test liquid 3 from the fuel injection valve 2 (i.e., an axial direction of the fuel injection valve 2, corresponding to a vertical direction in FIG. 1). An irradiation range of the light L from the irradiation device 7 to the spray 6 is set to a specific range which is a part of the spray 6 with respect to the injecting direction of the test liquid 3. On the other hand, an irradiation range with respect to the direction orthogonal to the injecting direction of the test liquid 3, in other words a width of the light L on a plane orthogonal to the injecting direction, is set so as to include a whole of the spray 6. In other words, the irradiation range of the light L is set such that the whole of the spray 6 passes through the irradiation range of the light L and spreads toward the collection container 8. Thereby, the light L is incident on all liquid drops contained in the spray 6 and the all liquid drops can be hardened. An irradiating position of the light L in the injecting direction can be varied along the injecting direction of the test liquid 3. For instance, the irradiation device 7 may be installed so as to move in whole or in part along the injecting direction of the test liquid 3, and by partially altering a light path within the irradiation device 7, the irradiating position may be changeable. With regard to the irradiating position of the light L, the center of the irradiation range with respect to the injecting direction of the test liquid 3 may be representative of the irradiating position.

The test apparatus 1 further includes a control unit 9. The control unit 9 controls operations of various instruments required for measurement of spray characteristics, such as a fuel injecting operation of the fuel injection valve 2, a pumping operation of the pump 5, an irradiating operation of the irradiation device 7, and the like. As the control unit 9, it is possible to use various control devices which are able to operate instruments to be controlled in a predetermined order, such as a programmable sequencer, a personal computer, or the like.

Figure 2:
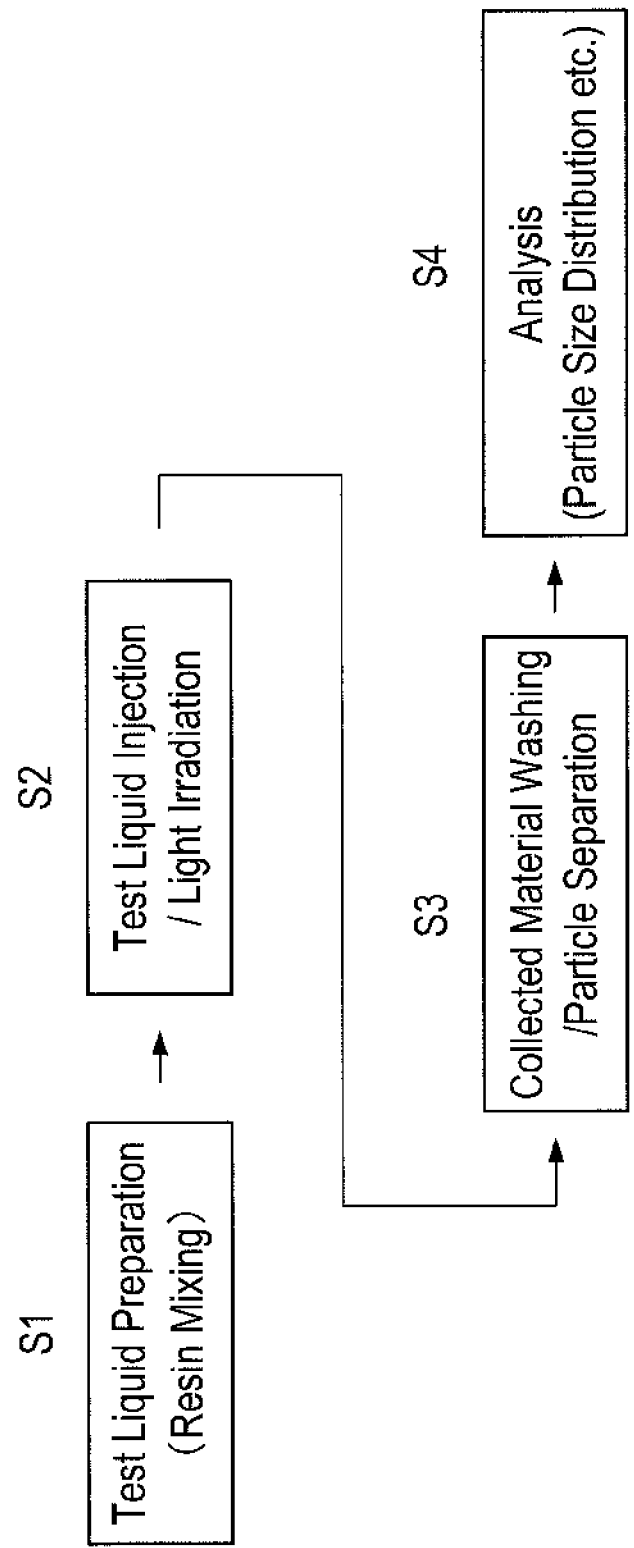
FIG. 2 is a flow diagram showing a procedure of a spray measuring method according to the first embodiment.

Next, a procedure of a measurement method of spray characteristics using the test apparatus 1 will be described with reference to FIG. 2. In the measurement method, firstly, the test liquid 3 is prepared by mixing the thermosetting resin to the fuel in a predetermined mixing ratio (step S1). The test liquid 3 is received in the tank 4. Next, the test liquid 3 is injected for a predetermined time by starting the operation of the pump 5 and driving the fuel injection valve 2, and the light L is irradiated from the irradiation device 7 at time which is at least apart of time when the spray can remain in synchrony with formation of the spray by the above injecting operation (step S2). That is, in the step S2, a process of injecting the test liquid is executed concurrently with a process of hardening the liquid drops into particles.

The injecting operation of the fuel injection valve 2, on-off control of the pump 5 and the irradiation time of the light L from the irradiation device 7 may be suitably controlled by the control unit 9. Control parameters for the fuel injection valve 2, e.g., a pressure of the test liquid 3, a driving duty ratio of the fuel injection valve 2, etc., may be set to the same values as when the fuel is actually injected from the fuel injection valve 2. Also environmental parameters such as a temperature and pressure under an environment in which the test liquid 3 is injected may be adjusted to conform to an environment in which the fuel injection valve 2 is actually arranged. The spray 6 injected from the fuel injection valve 2 including the particles hardened by irradiation of the light L, may be collected in the collection container 8 in sequential order. After completing the injection of the test liquid 3, the collected material in the collection container 8 is washed and the particles are separated from the collected material (step S3). A cleaning liquid to be used herein can be the test liquid 3. If using the test liquid 3 to wash the collected material, the hardened particles can be clearly separated from a liquid phase of the collected material. The cleaning liquid after use is recollected and then can be directly reused as the test liquid 3 in the next time. Alternatively, if the particles can be collected from the liquid phase without being washed, the washing process may be omitted.

After separating the particles, a predetermined analysis with regard to spray characteristics is executed by using the obtained particles (step S4). The step S4 substantially corresponds to a process of analyzing spray characteristics. In this case, for example, by measuring diameters of the obtained particles and processing statistically the measured values, it is possible to execute analysis such as measurement of a particle size distribution, measurement of an average diameter, and the like. The collected particles are obtained by hardening the liquid drops included in the spray 6. Accordingly, the measured particle size distribution may be considered to be substantially identical to a particle size distribution or an average diameter of the liquid drops included in the spray 6. Thereby, the spray characteristics of the fuel injection valve 2 can be easily measured with higher precision. By measuring a total weight of the test liquid 3 which is injected from the fuel injection valve 2 for one measurement in advance and calculating a difference between the total weight and a weight of all particles obtained above, an amount of a gas phase component in the spray 6 can be determined. Thereby, a ratio between the gas phase and liquid phase in the spray 6 can be identified.

According to the measurement method described above, by measuring only one time, it is possible to make the liquid drops included in the whole of the spray 6 harden and to measure a particle size distribution and the like of the liquid drops. Accordingly, compared to a measurement method such as analyzing the whole of the spray by repeating partial measurement of the spray, a result of measuring of the whole of the spray can be more efficiently obtained in a short time. Furthermore, in the above measurement method, it is possible to perform the measurement desired, if the light enters the whole of spray 6 within a part of the spray 6 with respect to the injecting direction, and an amount of the light is sufficient to harden the liquid drops. Thereby, even in a region in which the spray 6 is dense, spray characteristics can be easily measured. For instance, according to a method of observing transmitted light or reflected light by irradiating inspection light to the spray as a comparative example, light is attenuated in the region in which the spray is dense, and the transmitted light or reflected light required for observation cannot be obtained. This causes difficulties in measurement. On the other hand, according to the measurement method of the present embodiment, as described above, since it is enough if light enters the whole of the spray and an amount of light required for hardening is given, attenuation of light is not a problem. Accordingly, the measurement is possible even in a region in which the spray is dense. In the measurement method of the present embodiment, since the liquid drops in the spray are hardened by using the thermosetting resin, the collected particles are not dissolved by change in temperature or the like after collected, thus not returning to a liquid phase. Thereby, the particles can be easily handled during analysis. Since the above method is achieved by simply providing a device for irradiating light as a device for applying treatment to harden the liquid drops to the spray, it has advantages in aspects of simplification and downsizing of a test apparatus. By appropriately combining types of photocurable resin to be mixed with the test liquid 3, and a wavelength region and intensity of the light to be irradiated to the spray 6, a hardening reaction of the liquid drops in the spray 6 can be suitably controlled. Also, the spray 6 can be partially measured by irradiating the light L to only a part of the spray 6. Thereby, it is possible to promote diversification in measurement methods.

Figure 3:
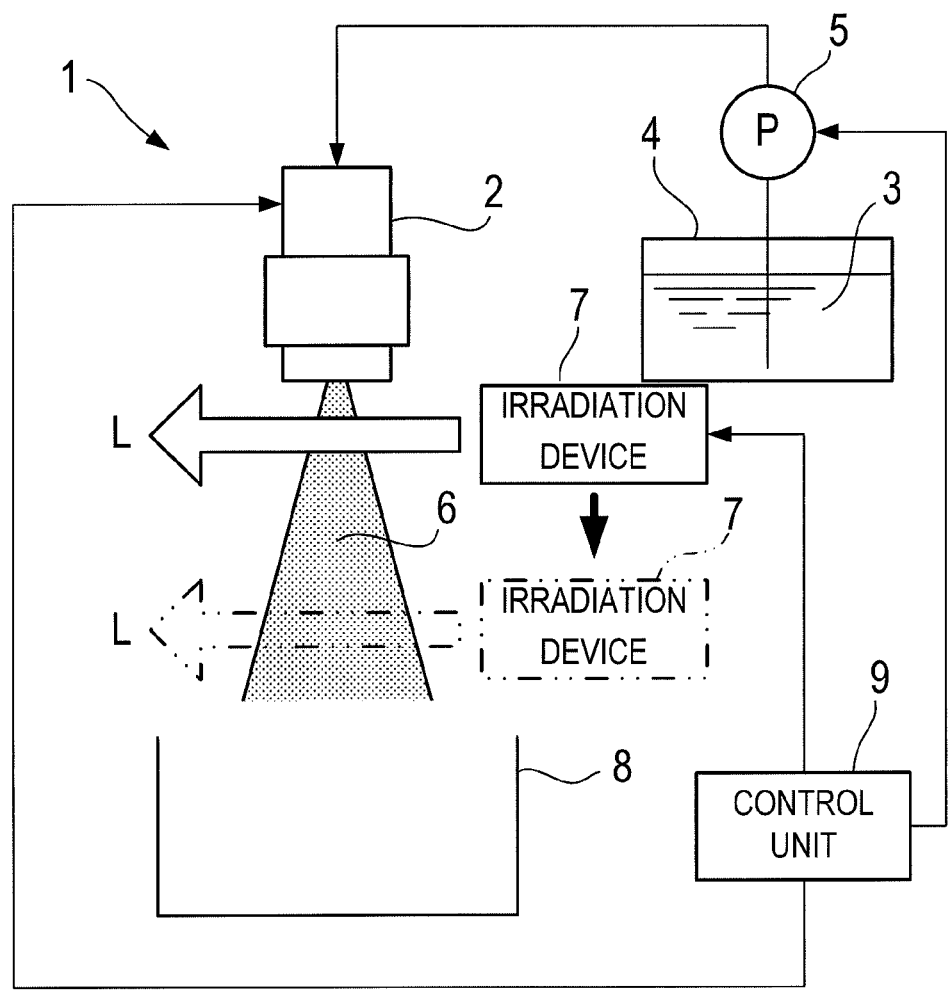
FIG. 3 is a diagram showing an example of changing an irradiating position of light.

With regard to the measurement method described above, the irradiating position and irradiation time of the light L to the spray 6 may be appropriately set. Whenever such measurement parameters are changed, the spray characteristics may be analyzed apart. For instance, as shown in FIG. 3, in one measurement, the irradiating position of the light L to the spray 6 is set near an injection port of the fuel injection valve 2. On the other hand, in another measurement, the irradiating position of the light L is set at a front end of the spray 6. Thus, the irradiating position of the light L may be changed for each measurement, and the spray characteristics may be analyzed for each irradiating position independently. In this case, the spray characteristics, such as the particle size distribution of the particles, the average diameter of the particles, and the like, can be analyzed in conjunction with the position of the spray 6. By comparison between analysis results at multiple positions, a positional variation of spray characteristics can be analyzed. However, for even a single measurement, if the irradiating position of the light L is sequentially altered while the test liquid 3 is continuously injected and the spray 6 (including hardened particles) is collected independently for each time the irradiating position is altered, analysis of spray characteristics for each irradiating position can be provided.

Figure 4:
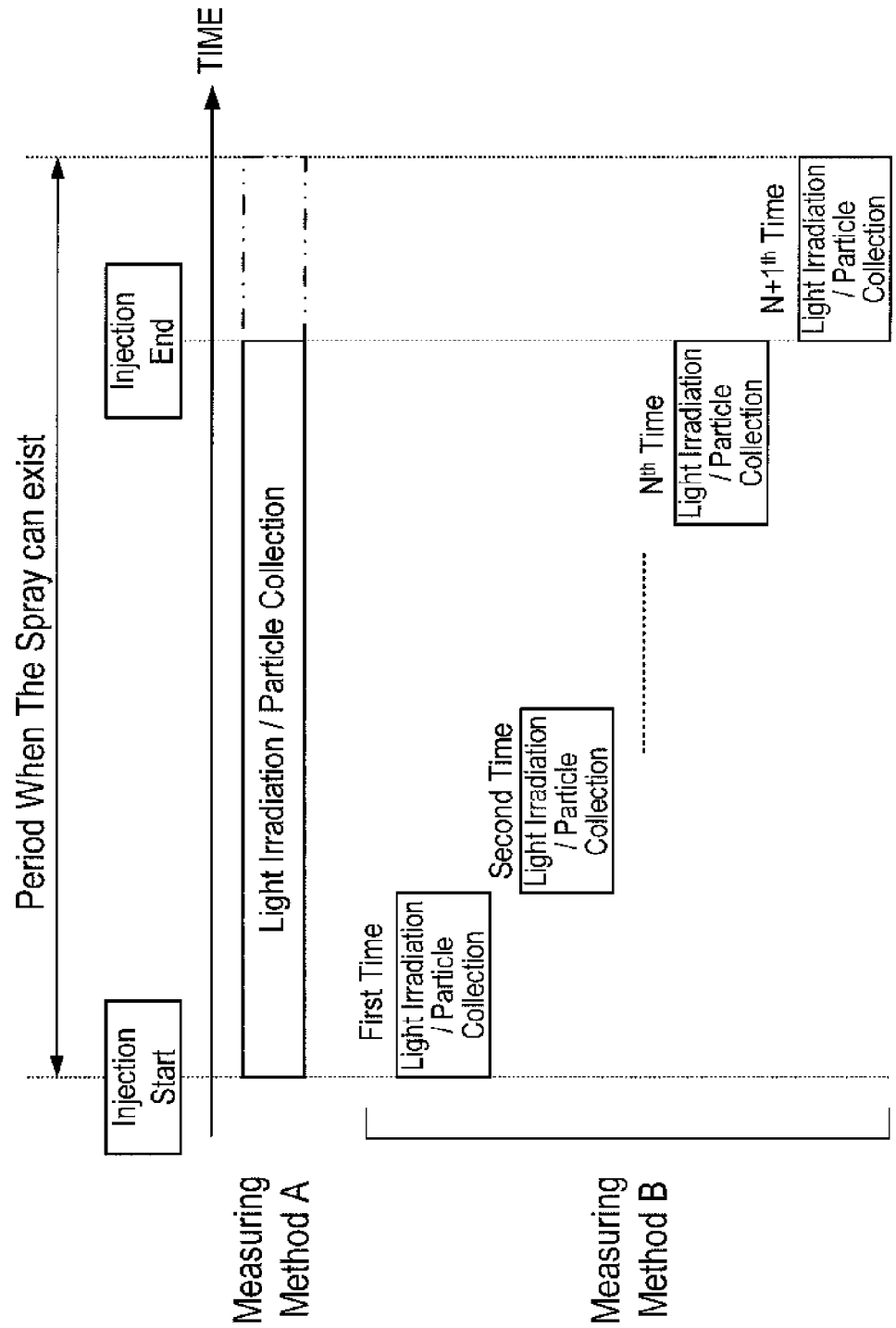
FIG. 4 is a diagram showing a relation between an injection period of a test liquid and an irradiation time of light.

With regard to the irradiation time, for example, like a measurement method A shown in FIG. 4, the light L may be continuously irradiated (including collection of particles) throughout an injection period ranging from the start of injection to the end thereof by a single measurement. However, the spray may sometimes remain for a certain time even after completing the injection. When the above spray is included in subjects to be measured, in the measurement method A, as illustrated in FIG. 4 with an imaginary line, a period ranging from the start of injection until a predetermined time has passed after completing the injection may be set as a period when the spray can exist, and the irradiation of the light L may be continued throughout the period. Otherwise, like a measurement method B, the irradiation time of the light L (including a collecting time of particles) in a single measurement may be limited to apart of the period when the spray can exist. The irradiation time may be set as a parameter that is controllable by the control unit 9. Thereby, the control unit 9 functions as an irradiation time control device. Furthermore, the setting of the irradiation time within the period when the spray can exist may be changed for every measurement, and spray characteristics may be analyzed separately for every irradiation time. In addition, in the measurement method B shown in FIG. 4, the light L is irradiated at a predetermined time after the start of the injection in a first measurement, in a second measurement, the light L is irradiated after a predetermined time from completing of the irradiation of the first measurement, and then the measurement is repeated in the same manner as described above while altering the irradiation time. In the measurement of the $N^{th}$ time (N is an integer of 3 or more), the light L is irradiated in a predetermined time, the end of which is set as end time of injection. Furthermore, by irradiating the light L at a predetermined time immediately after the end of injection, a measurement of the $N+1^{th}$ time is executed. However, in an example shown in FIG. 4, though the whole of the period when the spray can exist is divided into multiple irradiation times, a part of the period when the spray can exist may be divided into multiple irradiation times. For instance, first, middle and last stages in the period when the spray can exist may be suitably set up at constant intervals and each of the first, middle and last stages may be set to the irradiation time.

When the irradiation time of the light L is altered for each measurement in this way, analysis of spray characteristics can be performed in conjunction with a specific time in the period when the spray can exist. Also, by comparison between analyzed results for every irradiation time, a variation in the spray characteristics with respect to time may also be analyzed. For instance, if the spray characteristics from the start of injection are not constant, a variation in particle size distribution with respect to time and the like can be analyzed. However, even in a single measurement, by collecting the spray (including particles) separately for each appropriate time while continuously injecting the test liquid 3, it is possible to analyze spray characteristics according to the time during the period when the spray can exist. For instance, a variation in spray characteristics with respect to time may be substituted and determined as a position on the collection container 8 if the spray 6 is collected while the collection container 8 is moved in a direction orthogonal to the injecting direction.

Second Embodiment

Figure 5:
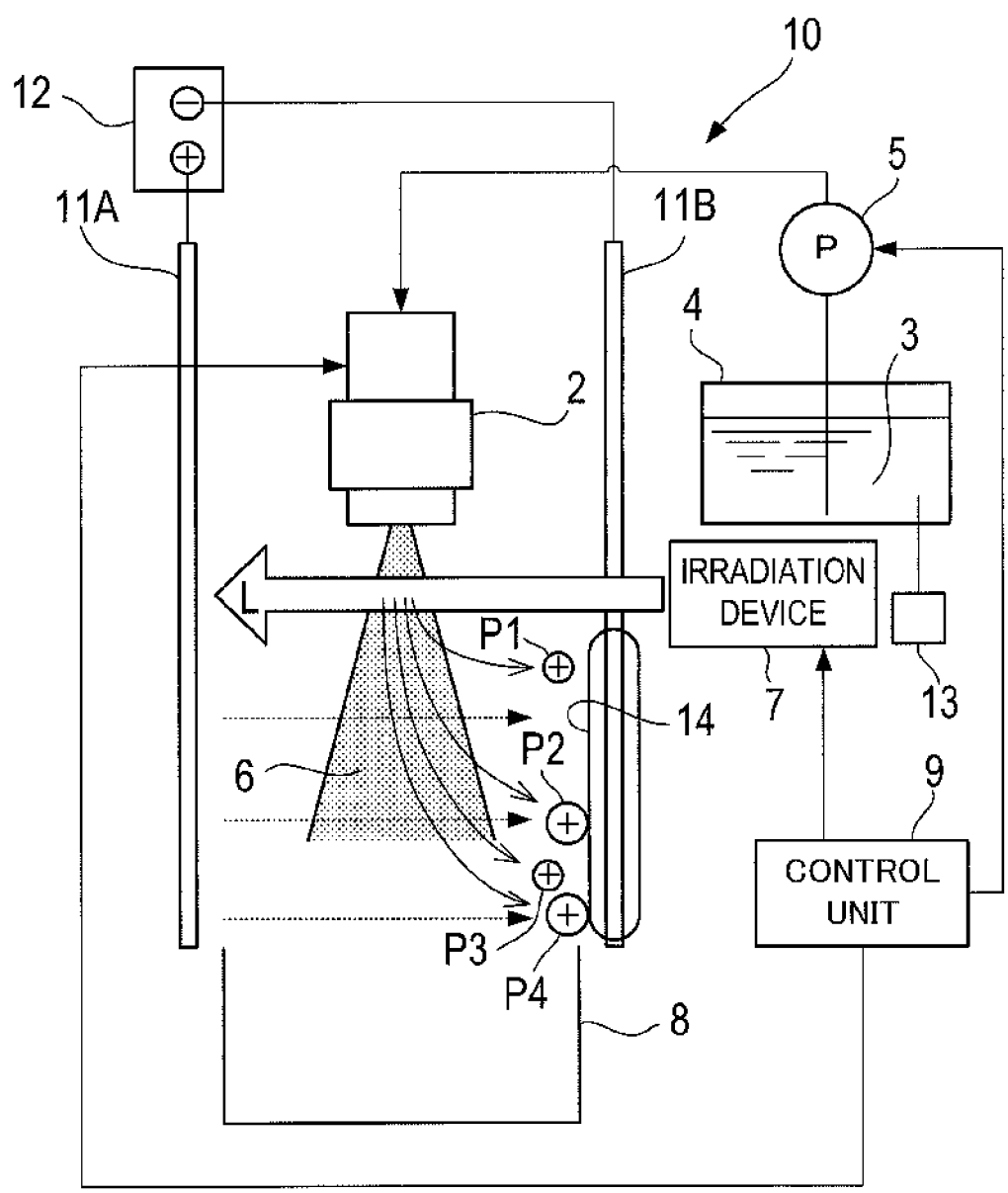
FIG. 5 is a diagram showing a test apparatus according to a second embodiment of the present invention.

FIG. 5 shows a schematic configuration of a test apparatus used in a spray measurement method according to a second embodiment of the present invention. However, in FIG. 5, the same components as those in the test apparatus 1 shown in FIG. 1 are denoted by the same reference numerals, and mainly differences will be described below. A test apparatus 10 in FIG. 5 has configurations of the test apparatus 1 shown in FIG. 1 as base configurations and additional configurations including a pair of electrodes 11A and 11B, a DC power supply 12 and a charging device 13. The electrodes 11A and 11B are arranged in parallel to face each other, so that the fuel injection valve 2 and a region where the test liquid 3 is injected from the fuel injection valve 2 are interposed in an irradiating direction of the light L. The one electrode 11A is connected to a positive electrode of the DC power supply 12 and the other electrode 11B is connected to a negative electrode of the DC power supply. By applying a voltage between the electrodes 11A and 11B from the DC power supply 12, as shown in FIG. 5 with a dashed arrow, it is possible to provide an electric field in parallel to the irradiating direction of the light L between the electrodes 11A and 11B.

The charging device 13 applies charge to the test liquid 3 contained in the tank 4 by imparting charge to the test liquid 3. For instance, the charging device is configured to execute charging treatment by flux. An operation for changing the test liquid 3 may be executed before irradiating the light L to the spray 6. For instance, the charging device 13 may be installed so that the test liquid 3 is charged on the way to the fuel injection valve 2 from the tank 4. Furthermore, the electrode 11B on the negative side is provided with a holding part 14 to hold particles adsorbed to the electrode 11B. The holding part 14 may be formed integrally with the electrode 11B. On the other hand, the holding part 14 may be formed as a separate member from the electrode 11B, and may be provided so as to function as a part of the electrode 11B substantially by being mounted on the electrode 11B. The electrode 11B has a hole or a window in order to make the light L pass from the irradiation device 7. Alternatively, the irradiation device 7 may be provided between the electrodes 11A and 11B.

Figure 6:
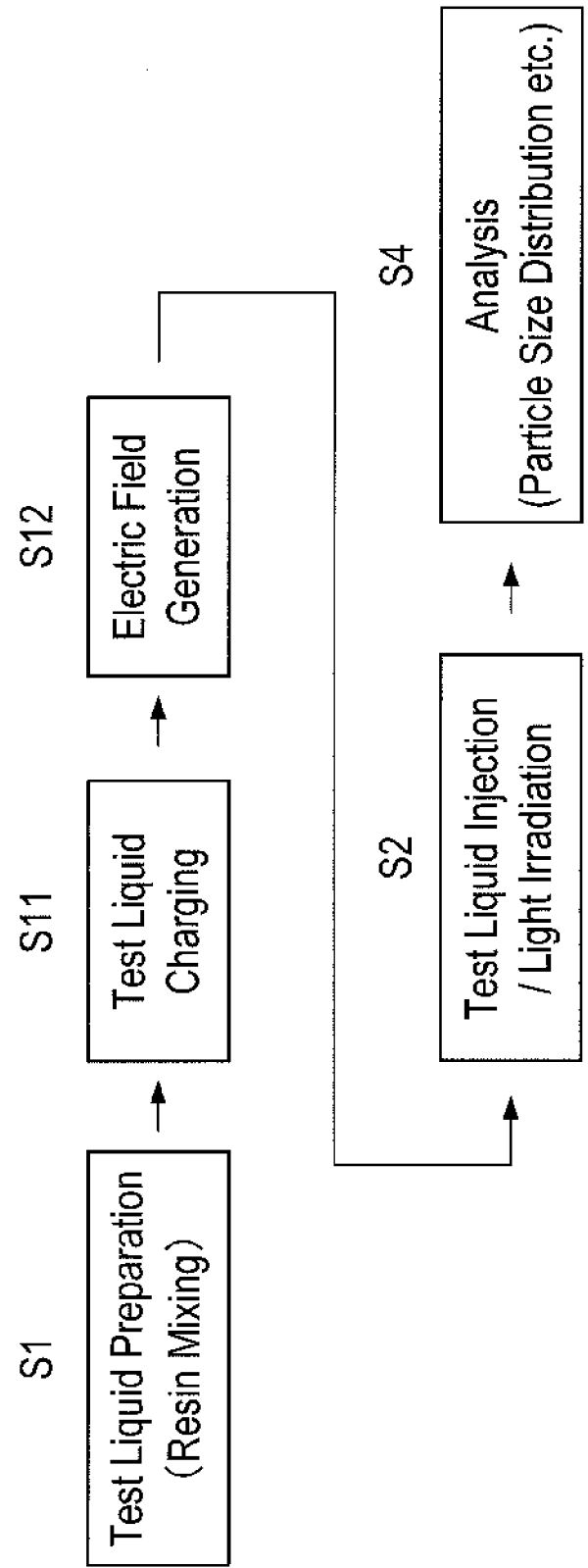
FIG. 6 is a flow diagram showing a procedure of a spray measuring method according to the second embodiment.

Next, a procedure of the measurement method of spray characteristics using the test apparatus 10 will be described with reference to FIG. 6. However, in FIG. 6, the same matters as those in the procedure shown in FIG. 2 are denoted by the same reference numerals, and mainly differences will be described below. In the measurement method shown in FIG. 6, the test liquid 3 is prepared and then treatment to charge the test liquid 3 by the charging device 13 is executed (step S11). For instance, the test liquid 3 is treated so as to have positive charge. The step S11 corresponds to a process of charging the test liquid. Then, a voltage is applied to the electrodes 11A and 11B from the DC power supply 12, and an electric field is applied to therebetween (step S12). Thereafter, as with the example in FIG. 2, injection of the test liquid 3 (step S2) and analysis of collected particles (step S4) are executed. Separation of particles from a liquid phase is not necessary.

According to the above method, a thermosetting resin contained in the test liquid 3 is hardened by irradiating the light L. Thereby, as with the above-described first embodiment, by collecting the particles, spray characteristics such as a particle size distribution, an average diameter of the particles, and the like, can be easily measured with higher precision. Moreover, since the test liquid 3 is injected in a positively charged state, the particles hardened by irradiation of the light L are attracted to the electrode 11B of the negative side and adsorbed to the holding part 14. An adsorption position (a reaching position) of a particle to the holding part 14 is a function of a mass and velocity of the particle, wherein the mass of the particle is determined by a diameter of the particle. Thereby, when the diameter of the particle is determined, it is possible to determine the velocity of the particle on the basis of the diameter and the adsorption position of the particle. In other words, individual particle is adsorbed and held at the holding part 14 in a distribution according to diameter and flow rate thereof. For instance, in FIG. 5, it is assumed that a particle P1 has a small diameter and a low velocity, a particle P2 has a large diameter and a low velocity, a particle P3 has a small diameter and a high velocity and a particle P4 has a large diameter and a high velocity. In this case, the particle P1 is adsorbed to the nearest position from the fuel injection valve 2. The particle P4 is adsorbed to the farthest position from the fuel injection valve 2. Since having a high velocity, the particle P3 is adsorbed to a farther position than the particle P1. Since having a low velocity, the particle P2 is adsorbed to a nearer position than the particle P4.

Accordingly, when a distribution of the particle groups held on the surface of the holding part 14 and a diameter of each particle held on the holding part 14 are measured, a velocity of each particle can be determined, and it is possible to measure a velocity distribution thereof. Therefore, more detailed measurement of spray characteristics can be performed. The distribution of the particle groups can be analyzed by, for example, photographing a whole image of the surface of the holding part 14. On the other hand, the diameter of each particle held on the holding part 14 can be analyzed by, for example, photographing an enlarged image of the holding part 14. An irradiation range of the light L is limited to a specific range of the spray 6 with respect to the injecting direction of the test liquid 3. Thereby, without considering a condition of liquid drops in the spray 6 before reaching the irradiation range, by measuring the distribution and diameter of the particles on the holding part 14, it is possible to determine a velocity of the particles. As with the above examples shown in FIG. 3 or 4, in the present embodiment, detailed measurement of spray characteristics may be executed by changing the irradiating position of the light L or by changing the irradiation time of the light L while restricting the irradiation time to apart of the period when the spray can exist.

The present invention is not limited to the above-described embodiments, and various modifications of the present invention can be provided. For instance, a variety of energy beam-curable resins such as photo-curable resins, electron beam-curable resins, etc., may be used instead of thermosetting resins as the curable resin included in the test liquid. That is, various resins can be suitably selected as the curable resin to be included in the test liquid as long as the resin is hardened by heat, a photochemical reaction or the like generated through irradiation of an energy beam such as a visible light, an ultraviolet ray, an X-ray, an electron beam, a heat-ray, etc. The energy beam to be irradiated from the irradiation device is not limited to light having a specific wavelength region such as ultraviolet light. The energy beam may be suitably changed in conjunction with the curable resin selected. Further, a resin which can be hardened by any treatment other than the irradiation of energy beam may also be used as the curable resin included in the test liquid. Treatment to be applied to the spray can be appropriately selected as long as they can make the curable resin harden.

The injection valve to be used in the test according to the present invention is not limited to a fuel injection valve of an internal combustion engine. Also, the liquid to be injected is not limited to the fuel. As long as liquid to be injected from a test liquid contains a curable resin and liquid drops in the spray can be hardened into particles by applying the treatment for producing a hardening effect to the spray, the spray measurement method and test apparatus of the present invention can be applied to measurement of spray injected from various types of injection valves.

The invention claimed is:

1. A spray measurement method comprising:
   a step of injecting test liquid including curable resin from an injection valve;
   a step of hardening liquid drops in a spray of the test liquid injected from the injection valve into particles by applying treatment for producing a hardening effect of the curable resin; and
   a step of analyzing spray characteristics of the injection valve using the particles hardened.

2. The spray measurement method according to claim 1, wherein
   the curable resin is a resin in which a hardening effect is produced by irradiation of an energy beam, and
   the energy beam is irradiated to the spray as the treatment in the step of hardening.

3. The spray measurement method according to claim 2, wherein
   a thermosetting resin is used as the curable resin, and
   light having a specific wavelength range is used as the energy beam.

4. The spray measurement method according to claim 2, wherein
   the irradiation of the energy beam to the spray is set to a partial region of the spray with respect to an injecting direction of the test liquid from the injection valve.

5. The spray measurement method according to claim 4, wherein
   while an irradiating position of the energy beam is changed along the injecting direction, the particles are analyzed each time the irradiating position being changed.

6. The spray measurement method according to claim 2, wherein
   irradiation time of the energy beam is limited to a part of a period when the spray of the test liquid exists.

7. The spray measurement method according to claim 2, wherein
   at least a part of the period when the spray of the test liquid exists is divided into several irradiation times,
   the energy beam is irradiated for each irradiation time, and
   the particles are analyzed separately for each divided irradiation time.

8. The spray measurement method according to claim 1, further comprising
   a step of charging the test liquid including the curable resin before applying the treatment to the spray, wherein
   in the step of hardening the liquid drops, an electric field is made to generate in a direction orthogonal to the injecting direction of the test liquid.

9. The spray measurement method according to claim 8, wherein
   in the step of hardening the liquid drops, the particles, a moving direction of which is curved by the electric field, are collected by being adsorbed and held on a holding part, the holding part being located along the injecting direction, and
   in the step of analyzing the spray characteristics, a distribution on the holding part and diameters of collected particles are measured, and a velocity distribution of the particles is determined based on the distribution and diameters of the particles obtained.

10. The spray measurement method according to claim 1, wherein
    the injection valve is a fuel injection valve of an internal combustion engine, and
    the test liquid is prepared by mixing the curable resin with fuel of the internal combustion engine.

11. A spray test apparatus comprising:
    a test liquid supply device which is configured to supply a test liquid including curable resin to an injection valve; and a hardening device which is configured to harden liquid drops in a spray of the test liquid injected from the injection valve into particles by applying treatment for producing a hardening effect to the curable resin, to the spray, wherein the test liquid supply device is configured to supply to the injection valve the test liquid containing the curable resin in which a hardening effect is produced by irradiation of an energy beam, and the hardening device is configured to irradiate the energy beam to the spray as the treatment.

12. The spray test apparatus according to claim 11, wherein the test liquid supply device is configured to supply thermosetting resin, as the curable resin, to the injection valve, and the hardening device is configured to irradiate light having a specific wave length range as the energy beam.

13. The spray test apparatus according to claim 11, wherein the hardening device is configured so that the irradiation of the energy beam is limited to a part of the spray in an injecting direction of the test liquid from the injection valve.

14. The spray test apparatus according to claim 13, wherein the hardening device is configured to be capable of changing an irradiating position of the energy beam along the injecting direction.

15. The spray test apparatus according to claim 11, further comprising an irradiation time control device which is configured to restrict irradiation time of the energy beam to at least a part of a period when the spray of the test liquid can exist.

16. The spray test apparatus according to claim 11, further comprising a charging device which is configured to charge the test liquid including the curable resin, and an electric field generation device which is configured to generate an electric field in a direction orthogonal to the injecting direction of the test liquid.

17. The spray test apparatus according to claim 16, wherein the electric field generation device has a pair of electrodes arranged to face each other so that a region where the test liquid is injected is interposed in a direction orthogonal to the injecting direction, and the electrode having opposite polarity to a charge of the test liquid, is provided with a holding part adsorbing and holding particles, a moving direction of the holding particles being curved by the electric field.

* * * * *